United States Patent [19]

Sandford et al.

[11] Patent Number: 5,451,876
[45] Date of Patent: Sep. 19, 1995

[54] MRI SYSTEM WITH DYNAMIC RECEIVER GAIN

[75] Inventors: Lorraine V. Sandford, Champaign, Fla.; Joseph K. Maier, Milwaukee; Robert S. Stormont, Waukesha, both of Wis.

[73] Assignee: General Electric Company, Milwaukee, Wis.

[21] Appl. No.: 138,273

[22] Filed: Oct. 18, 1993

[51] Int. Cl.[6] .............................................. G01V 3/00
[52] U.S. Cl. ..................................... 324/322; 324/314
[58] Field of Search ............... 324/300, 307, 309, 313, 324/314, 318, 322; 128/653.5

[56] References Cited

U.S. PATENT DOCUMENTS 4,700,138  10/1987  Shimazaki et al. ................... 324/322
4,806,866   2/1989  Maier .................................... 324/313

OTHER PUBLICATIONS

Effective Dynamic Range Improvement of NMR Signal Detection by Using Analog Programmable Attenuators, C. H. Oh, et al., *SMRM Eighth Annual Meeting*, (1989), p. 181.

*Primary Examiner*—Louis M. Arana
*Attorney, Agent, or Firm*—Quarles & Brady

[57] ABSTRACT

An NMR system includes a transceiver which receives NMR signals of varying amplitude during a scan. The gain of the receiver is dynamically changed during the scan to provide an optimal SNR figure without overranging the transceiver's A/D converter. The acquired NMR signals are normalized prior to image reconstruction using correction factors for gain and phase stored in a normalization table.

6 Claims, 3 Drawing Sheets

MRI SYSTEM WITH DYNAMIC RECEIVER GAIN

BACKGROUND OF THE INVENTION

The field of the invention is nuclear magnetic resonance imaging methods and systems. More particularly, the invention relates to the adjustment of receiver gain to obtain low-noise images under varying signal conditions.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated and this signal may be received, digitized and processed to form an image.

When utilizing these signals to produce images, magnetic field gradients ($G_x$ $G_x$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

The amplitude of the received NMR signal used to reconstruct an image will vary greatly depending on a number of factors. For example, the NMR signal amplitude will increase with increased slice thickness, increased pulse repetition time (TR), decreased echo time (TE) increased patient size, increased fat content in patient and choice of receiver coil (i.e. whole body coil, surface coil, head coil, etc.). These factors remain relatively constant during the scan and the receiver gain is typically set to a single value during a prescan process, which insures that the peak NMR signal amplitude will not over-range the analog-to-digital converter. Such a prescan is disclosed, for example, in U.S. Pat. No. 4,806,866 entitled "*Automatic RF Frequency Adjustment For Magnetic Resonance Scanner*".

The quality of the reconstructed image is related to its signal-to-noise ratio (SNR), and this SNR may be degraded when the receiver gain is lowered to handle the largest signals. This occurs because the noise figure within the MRI system receiver increases as the receiver gain decreases. During a typical scan the NMR signals from different views will have a range of amplitudes and the receiver gain is fixed at a value which utilizes the full range of the analog-to-digital converter when the maximum expected signal amplitude is received. This means that many low level NMR signals are acquired during the scan without utilizing the full range of the analog-to-digital converter, yet have less than the optimal SNR figure. For example, views with minimal phase encoding gradients applied have high amplitudes and must be acquired with low system gain yielding a less than optimal noise figure. The views acquired with high phase encoding gradients, on the other hand, have small amplitudes, but are acquired with a system noise figure set for the largest signal conditions.

SUMMARY OF THE INVENTION

The present invention relates to an improved MRI system in which the receiver gain is dynamically adjusted during a scan to optimize the SNR for each received NMR signal. Prior to image reconstruction the NMR signals thus acquired are adjusted to normalize out the differences in amplitude and phase caused by the changing receiver gain settings. More particularly, each NMR signal is acquired during the scan with an associated receiver gain setting that is determined as a function of a scan parameter, each acquired NMR signal is normalized using a value selected from a stored normalization table, and an image is reconstructed from the normalized NMR signals acquired during the scan. One such scan parameter, for example, is phase encoding magnetic field gradient amplitude, and the receiver gain settings increase as a function of increasing phase encoding.

A general object of the invention is to increase the SNR of MR images. This is accomplished by more efficiently utilizing the full range of the analog-to-digital converter for acquired NMR signals of vastly different amplitudes. Variations in NMR signal amplitude are related to a scan parameter, and the scan parameter is used to select a receiver gain that will fully utilize the analog-to-digital converter range. For example, the scan parameter may be phase encoding value, or it may be a signal indicative of patient respiration or other body function which causes a predictable change in NMR signal amplitude.

A more specific object of the invention is to normalize NMR signals acquired during a scan with different receiver gains. A normalization table stores an amplitude correction and a phase correction value for each possible receiver gain setting. The receiver gain setting associated with each acquired NMR signal is used to select the proper amplitude and phase correction values from this normalization table, and these are applied to normalize the NMR signal.

DESCRIPTION OF THE PREFERRED EMBODIMENT

Figure 1:
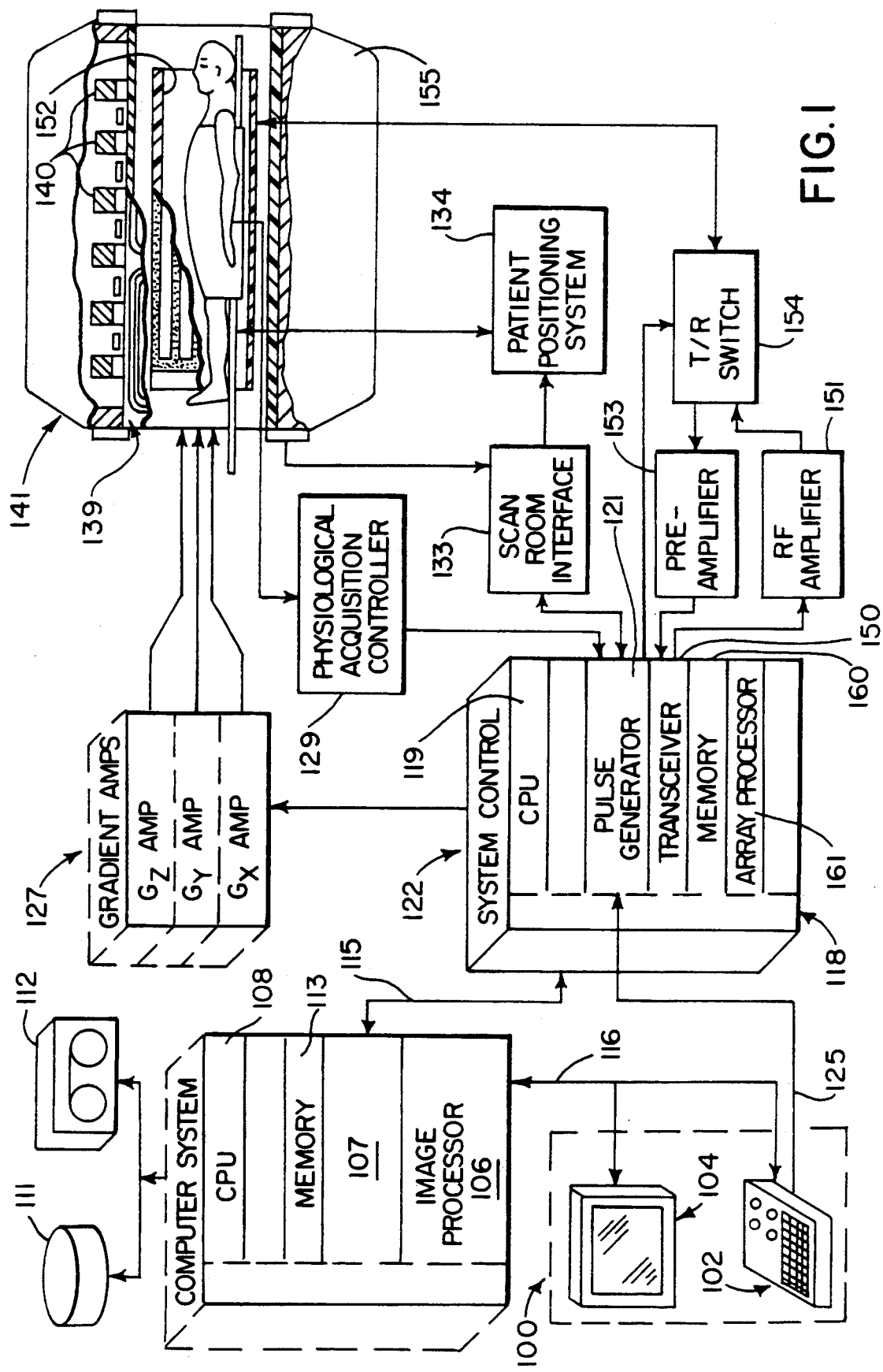
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152.

A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
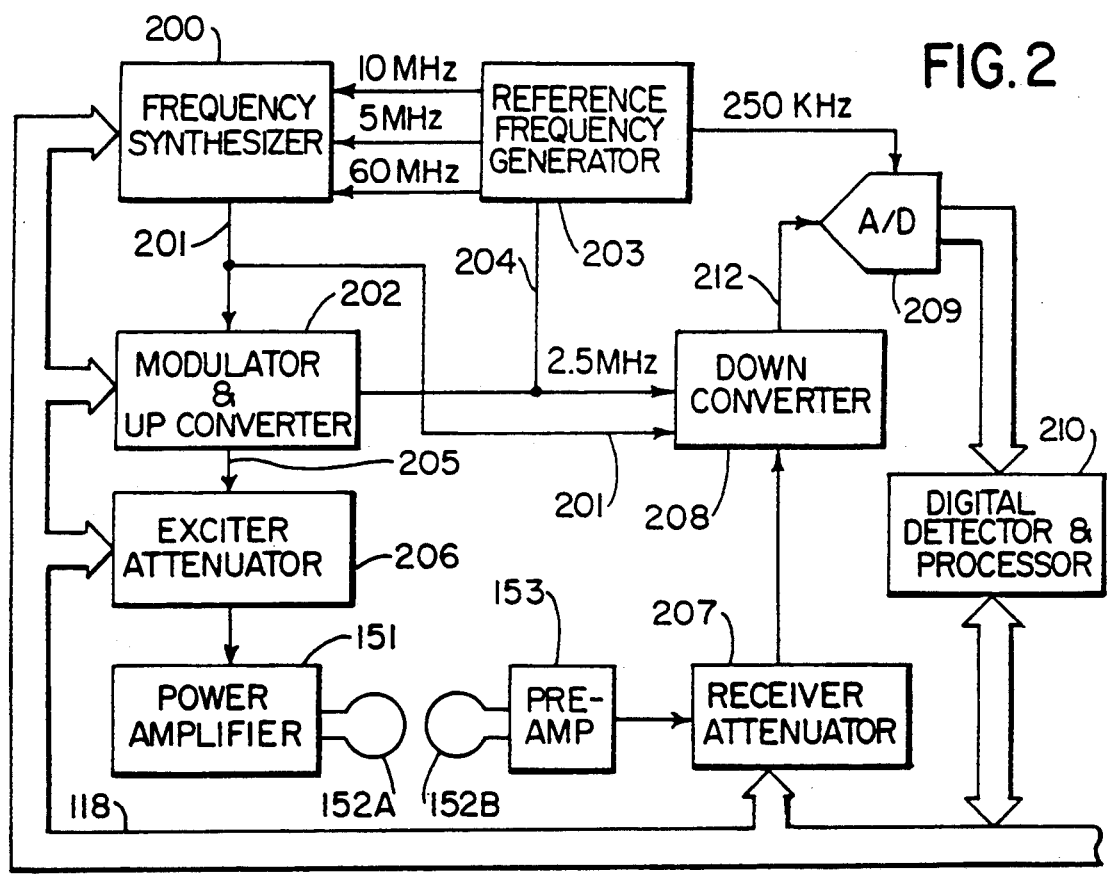
FIG. 2 is an electrical block diagram of the transceiver which forms part of the MRI system of FIG. 1.

Referring particularly to FIGS. 1 and 2, the transceiver 150 produces the RF excitation field $B_1$ through power amplifier 151 at a coil 152A and receives the resulting signal induced in a coil 152B. As indicated above, the coils 152A and B may be separate as shown in FIG. 2, or they may be a single wholebody coil as shown in FIG. 1. The base, or carrier, frequency of the RF excitation field is produced under control of a frequency synthesizer 200 which receives a set of digital signals (CF) from the CPU module 119 and pulse generator module 121. These digital signals indicate the frequency and phase of the RF carrier signal produced at an output 201. The commanded RF carrier is applied to a modulator and up converter 202 where its amplitude is modulated in response to a signal R(t) also received from the pulse generator module 121. The signal R(t) defines the envelope of the RF excitation pulse to be produced and is produced in the module 121 by sequentially reading out a series of stored digital values. These stored digital values may, in turn, be changed from the operator console 100 to enable any desired RF pulse envelope to be produced.

The magnitude of the RF excitation pulse produced at output 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIG. 1 and 2 the NMR signal produced by the subject is picked up by the receiver coil 152B and applied through the preamplifier 153 to the input of a receiver attenuator 207. The receiver attenuator 207 further amplifies the signal by an amount determined by a digital attenuation signal (RA) received from the backplane 118. It is this attenuation signal (RA) that is employed to dynamically adjust the receiver gain during a scan in accordance with the preferred embodiment of the invention.

The received signal is at or around the Larmor frequency, and this high frequency signal is down converted in a two step process by a down converter 208 which first mixes the NMR signal with the carrier signal on line 201 and then mixes the resulting difference signal with the 2.5 MHz reference signal on line 204. The down converted NMR signal is applied to the input of an analog-to-digital (A/D) converter 209 which samples and digitizes the analog signal and applies it to a digital detector and signal processor 210 which produces 16bit in-phase (I) values and 16-bit quadrature (Q) values corresponding to the received signal. The resulting stream of digitized I and Q values of the received signal are output through backplane 118 to the memory module 160 where they are normalized in accordance with the present invention and then employed to reconstruct an image.

The 2.5 MHz reference signal as well as the 250 kHz sampling signal and the 5, 10 and 60 MHz reference signals are produced by a reference frequency generator 203 from a common 20 MHz master clock signal. For a more detailed description of the receiver, reference is made to U.S. Pat. No. 4,992,736 which is incorporated herein by reference.

The present invention is implemented by changing the digital attenuation signal (RA) applied to the receiver during the scan so that NMR signals of widely varying amplitude can be acquired at an improved SNR. After each NMR signal is acquired, therefore, its measured amplitude must be adjusted to account for the particular receive attenuation (RA) used during its acquisition. This adjustment, or "normalization" of the NMR signal amplitudes insures that the relative amplitudes of the NMR signals employed to reconstruct an image are maintained and they each contribute accurately to the reconstructed image. As will be described below, the amplitude adjustments are made by multiplying the acquired signal by a factor (A) which normalizes it with an NMR signal acquired at the optimal receiver attenuation value (RA).

Because the NMR signals are Fourier transformed during the image reconstruction process, the relative phase of the acquired signals must also be maintained. While it is possible to construct a signal attenuator with little or no variation in phase shift between settings, as a practical matter this is not desirable. Thus, practical receivers not only change the amplitude of the acquired NMR signal as a function of the attenuation value (RA), but they also change the time delay imposed on the signal. These time delays must be normalized to preserve the relative phases of all the NMR signals employed to reconstruct an image. Otherwise, the image resolution is reduced due to smearing, or blurring, caused by misplacement of spin signals along the readout gradient axis.

Figure 3A:
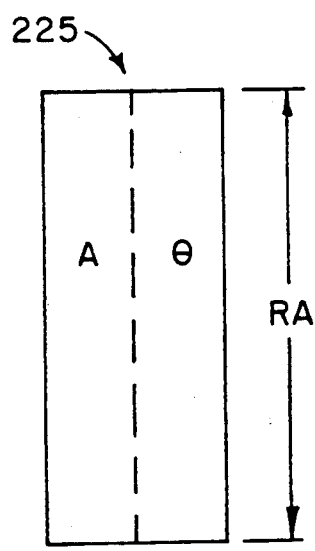
FIGS. 3A and 3B are schematic representations of two preferred embodiments of a normalization table stored in the MRI system of FIG. 1 and employed to practice the present invention.
Figure 3B:
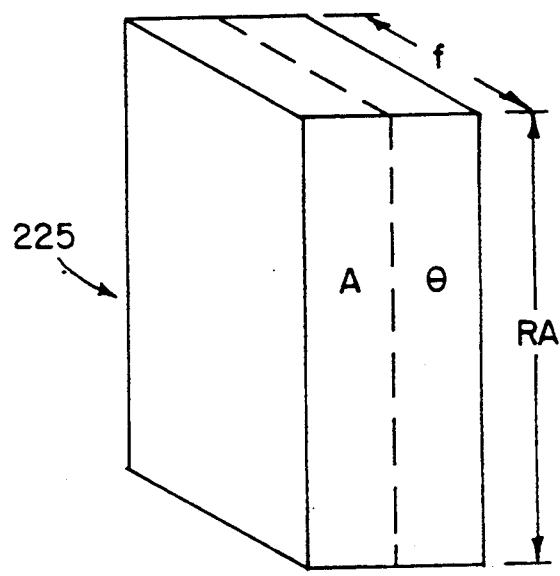

Referring particularly to FIGS. 1, 3A and 3B, as each NMR signal is acquired by the transceiver 150 it is stored as an array of complex numbers in the memory module 160. Each of these complex numbers indicates the phase and amplitude of a time domain sample of the NMR signal. As will be described in more detail below, the CPU module 119 operates on this acquired NMR signal to normalize its amplitude and phase in accordance with respective correction factors (A) and ($\theta$) stored in a normalization table 225 contained in memory module 160.

One preferred embodiment of this normalization table 225 is shown in FIG. 3A and stores time domain corrective values A and $\theta$ for each possible receive attenuation value (RA). The attenuation value RA at which the stored NMR signal was acquired is employed as an index into this table 225, and the corrective factors A and $\theta$ are read out and employed to correct each time domain NMR signal sample $(I_t, Q_t)$ as follows:

$$I_n = I_t(A)\cos\theta - Q_t(A)\sin\theta$$

$$Q_n = I_t(A)\sin\theta + Q_t(A)\cos\theta \tag{1}$$

The resulting normalized NMR signal $(I_n, Q_n)$ is then transferred to the array processor 161 which performs the Fourier transformations necessary to reconstruct an image.

A second preferred embodiment of the normalization table 225 is shown in FIG. 3B and stores frequency domain corrective values A and $\theta$ for each possible receive attenuation value (RA) and at each discrete frequency of a Fourier transformed NMR signal. In this embodiment of the invention the acquired NMR signal is first Fourier transformed to the frequency domain by the array processor 161 and stored in memory 160 as an array of complex values in discrete frequency "bins". The attenuation value RA at which the stored NMR signal was acquired is employed as one index into the normalization table 225 of FIG. 3B, and the frequency bin number (f) of a particular NMR signal value is used as a second index to read out the proper correction factors A and $\theta$. The correction factors A and $\theta$ are applied to alter the amplitude and phase of the frequency domain NMR signal samples $(I_f, Q_f)$ to produce normalized samples $(I_n, Q_n)$ as indicated above in equation (1). After all the signal values have been separately corrected, the normalized frequency domain NMR signal is conveyed to the array processor 161 to complete the image reconstruction process. This second embodiment of the invention is preferred when the phase or the amplitude changes imposed on the NMR signal by the receiver are not only dependent on the receive attenuation RA, but also are significantly frequency dependent. In other words, when the phase correction $\theta$ is not relatively constant for each receive attenuation setting (RA), or amplitude the correction (A) is frequency dependant, the more complex method is preferred.

The corrective values A and $\theta$ in the normalization table 225 are determined for each receiver as part of a calibration process and remain fixed. The normalization table 225 of FIG. 3A is produced by applying a sine wave of constant amplitude $A_0$ and sampling this signal at each possible receive attenuation setting RA. The corrective values for the normalization table 225 of FIG. 3B are produced in a similar manner, but for each attenuation setting (RA) the frequency of the applied sine wave also is swept through the entire set of readout gradient axis frequencies. In either case the received signal is Fourier transformed to the frequency domain and the complex value $(I_f, Q_f)$ in the frequency bin corresponding to the frequency of the applied sine wave is used to calculate the corrective values for that RA setting and frequency bin as follows:

$$A = A_{nom}/\sqrt{I_f^2 + Q_f^2} \tag{2}$$

$$\theta = \theta_{nom} - \tan^{-1}(Q_f/I_f)$$

where $A_{nom}$ and $\theta_{nom}$ are the amplitude and phase of the values produced in the same frequency bin by the applied signal measured with RA set to its optimal value from a receiver noise standpoint. The corrective values determined by this receiver calibration process are stored as normalization table 225 in memory module 160 and are used during any subsequent scan in which receiver attenuation (RA) is dynamically changed.

It should be apparent to those skilled in the art that when a plurality of receivers are used in parallel, as with a phase array receive coil, a separate normalization table 225 may be created for each and used separately in the subsequent scans.

Figure 4:
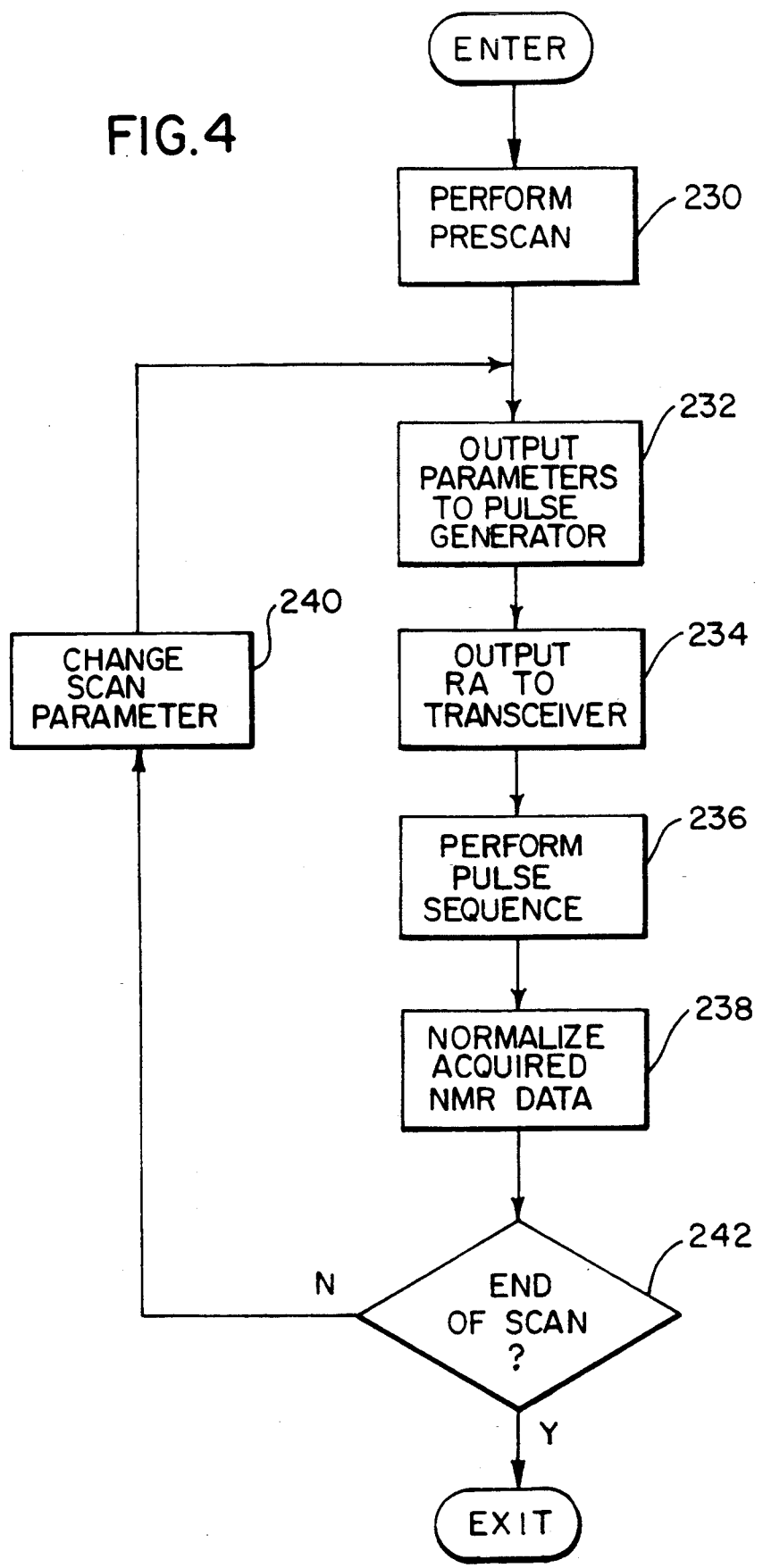
FIG. 4 is a flow chart of a program executed by the MRI system of FIG. 1 to practice the present invention.

Referring particularly to FIG. 4, the CPU module 119 directs the data acquisition process during a scan in accordance with a stored program. As indicated by process block 230, a prescan is performed first in which NMR data is acquired from which the transceiver is calibrated as is well known in the art. As will be discussed in more detail below, NMR data may also be acquired at this time to determine how NMR signal amplitude will vary during the scan as a function of certain scan parameters such as phase encoding value, slice select location and echo time TE. This information is used to build a table of RA settings which are output to the transceiver 150 as the scan is "played out" and these scan parameters are changed.

After the prescan 230, a loop is entered in which scan parameters are output to the pulse generator 121 at process block 232. The appropriate receive attenuation value RA is output to transceiver 150 at process block 234, and the programmed pulse sequence is then initiated as indicated at process block 236 to acquire an NMR signal which is stored in memory module 160 as described above. As indicated at process block 238, this acquired NMR signal is then normalized using one of the above-described procedures and the data is passed to the array processor 161 for image reconstruction. This process repeats after changing the scan parameters at process block 240 until all the NMR signals required by the scan protocol have been acquired as determined at decision block 242. The completed scan is indicated and the image, or images are reconstructed and made available to the operator for viewing or further processing.

The table of receiver attenuation values (RA) used during the scan can be produced in a number of ways. Such a table may be constructed, for example, by executing the pulse sequence with no phase encoding, and setting the receive attenuation ($RA_0$) for an optimal signal level ($A_0$). The pulse sequence is then repeated with phase encoding applied to measure the NMR signal level (A). The value of receive attenuation (RA) required to produce the optimal signal level ($A_0$) is then calculated as follows:

$$RA = RA_0(A/A_0) \qquad (4)$$

This may be repeated for each phase encoding value used during the scan, or preferably, only a few values are measured and RA settings for all possible phase encodings are determined by interpolating between the calculated RA settings. Regardless of the precise method used, the resulting table of RA values is stored in the memory module 160 and is used to set the receiver attenuation during the subsequent scan.

A similar method may be employed to calculate other receive attenuation tables for use during the scan. For example, if multiple slices are acquired during the scan over a range of human anatomy that produces vastly different signal levels, the signal level is sampled from each slice during the prescan. From these measurements a receive attenuation table is produced which may be used during the subsequent scan to dynamically adjust receiver gain.

It should be apparent to those skilled in the art that the receive attenuation can be adjusted dynamically during the scan as a function of more than one scan parameter. This is accomplished by multiplying the receive attenuation values from corresponding receive attenuation tables, and applying the combined values to the transceiver 150 during the scan. This combined value is then used, of course, during the subsequent normalization process.

We claim:

1. In an NMR system a method for reconstructing an image from a plurality of acquired NMR signals, the steps comprising:
    a) storing a normalization table comprised of a plurality of amplitude and phase corrections ($A,\theta$), each of the amplitude and phase corrections being associated with one of a corresponding plurality of receiver attenuation values (RA);
    b) acquiring one of said NMR signals with a receiver whose gain is set by one of said receiver attenuation values (RA);
    c) normalizing the acquired NMR signal by altering its amplitude and phase by an amount determined by the amplitude and phase corrections ($A,\theta$) in the normalization table associated with said one of said receiver attenuation values (RA);
    d) repeating steps b) and c) to acquire further NMR signals with the receiver gain set by different ones of said receiver attenuation values (RA); and
    e) reconstructing an image using the normalized, acquired NMR signals.

2. The method as recited in claim 1 in which the acquired NMR signal is normalized in step c) by multiplying its amplitude by the amplitude correction (A) and shifting its phase by an amount determined by the phase correction ($\theta$).

3. The method as recited in claim 1 in which each NMR signal acquired in step b) is Fourier transformed prior to its normalization in step c).

4. The method as recited in claim 1 in which the different ones of said receiver attenuation values (RA) are selected as a function of a parameter which changes value during the acquisition of said plurality of NMR signals.

5. The method as recited in claim 4 in which the parameter is the value of a phase encoding gradient field which is produced by the NMR system.

6. The method as recited in claim 4 in which the parameter is the location of a slice from which the NMR signal is produced.

* * * * *